United States Patent [19]

Kern

[11] Patent Number: 4,885,310

[45] Date of Patent: Dec. 5, 1989

[54] ANTI-FUNGAL METHODS AND AGENT

[75] Inventor: Gerald N. Kern, 4631 Louis Ave., Encino, Calif. 91316

[73] Assignee: Gerald N. Kern, Encino, Calif.

[21] Appl. No.: 732,876

[22] Filed: May 9, 1985

[51] Int. Cl.$^4$ .......................................... A61K 31/225
[52] U.S. Cl. .................................................... 514/547
[58] Field of Search .......................................... 514/547

[56] References Cited

U.S. PATENT DOCUMENTS

| | | | |
|---|---|---|---|
| 2,028,091 | 1/1936 | Jaeger | 260/106 |
| 2,149,240 | 2/1939 | Crossley | 514/547 |
| 2,176,423 | 10/1939 | Jaeger | 260/481 |
| 2,574,526 | 11/1951 | Bordon et al. | 117/86 |
| 3,650,964 | 3/1972 | Sedliar et al. | 252/106 |
| 3,737,552 | 6/1973 | Gordon et al. | 514/547 |
| 3,873,721 | 3/1975 | Hargett | 514/547 |
| 3,942,512 | 3/1976 | Hargett | 514/547 |
| 3,984,570 | 10/1976 | Bent et al. | 424/390 |
| 4,013,418 | 3/1977 | Plakas | 23/253 |
| 4,066,786 | 1/1978 | Bent et al. | 424/313 |
| 4,096,311 | 6/1978 | Pietreniak | 428/289 |
| 4,148,872 | 4/1979 | Wagenknecht et al. | 424/48 |
| 4,156,715 | 3/1979 | Wagenknecht et al. | 424/48 |
| 4,156,716 | 3/1979 | Wagenknecht et al. | 424/48 |
| 4,157,385 | 6/1979 | Wagenknecht et al. | 424/48 |
| 4,161,517 | 9/1979 | Wagenknecht et al. | 424/48 |
| 4,307,143 | 12/1981 | Meitner | 252/91 |
| 4,334,910 | 6/1982 | Lorimez et al. | 71/82 |
| 4,387,107 | 6/1983 | Klein et al. | 424/338 |
| 4,514,385 | 4/1985 | Damani et al. | 424/81 |
| 4,540,566 | 9/1985 | Davis et al. | 424/22 |
| 4,578,265 | 3/1986 | Pellico et al. | 424/50 |

FOREIGN PATENT DOCUMENTS

| | | |
|---|---|---|
| 0107594 | 5/1984 | Fed. Rep. of Germany ...... 514/547 |
| 53-113019 | 10/1978 | Japan . |
| 56-15202 | 2/1981 | Japan . |
| 2103089 | 7/1982 | United Kingdom ................ 514/547 |
| 2103089A | 2/1983 | United Kingdom ................ 514/547 |

OTHER PUBLICATIONS

A. G. Gilman, L. S. Goodman and A. Gilman, The Pharmacological Basis of Therapeutics (1980), Sixth Edition, pp. 1008–1009.

Department of Health and Human Services Food and Drug Administration, Report Docket No. 84N-0184, "Dioctyl Sodium Sulfosuccinate, Dioctyl Potassium Sulfosuccinate, and Dioctyl Calcium Sulfosuccinate"; Availability of the Final Report of the DSS Scientific Review Panel, Mar. 1984.

"Injury of Bacteria by Sanitizers", D. L. Scheusner et al., (Dept. of Food Sci., North Carolina State University, Raleigh, N.C.) Appl. Microbiol. 1971, 21(1), 41–5.

"Bloat in Cattle, XVI. Development and Application of Techniques for Selecting Drugs to Prevent Feedlot Bloat," R. M. Meyer et al., (Kansas Agric. Exp. Stn. Kansas State Univ. Manhattan, Kan.), J. Admin. Sci. 1972, 34(2), 234–40.

Baker et al., "Action of Synthetic Detergents on the Metabolism of Bacteria," J. Exp. Med., 73 2490271, (1941).

Chemical Abstract (56:9226g), Belgian article titled, "Bactericidal Properties of Anionic Detergents".

(List continued on next page.)

Primary Examiner—Jerome D. Goldberg
Attorney, Agent, or Firm—Christie, Parker & Hale

[57] ABSTRACT

Methods and compositions are provided for treating selected fungal infections wherein the anti-fungally active ingredient is a compound of the following formula:

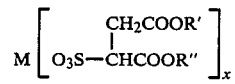

wherein R' and R" are each independantly a straight chain or branched chain alkyl group of from 5 to 8 carbon atoms, M is NH4, Na, K, Ca, and x is 1 when M is Na, K or NH4, and x is 2 when M is Ca.

26 Claims, 1 Drawing Sheet

OTHER PUBLICATIONS

"Studies of the Anti-Microbial Activity of Nonionic and Anionic Surfactants", Chuichi Ishizeki, (Eisei Shikensho, Japan), Eisei Shikenjo Hokoku, 1970, (88) 75-8.
Accepted Dental Therapeutics, 35th Ed., published by the American Assocation, Chicago, 1973, p. 265.
"Spraying Potatoes to Prevent Leaf Roll Spread by the Green Peach Aphid", W. A. Shands et al., (Univ. Maine, Orono, Maine), Amer. Potato J. 1972 49(1), 23-34.
"Effects of Several Wetting Agents on the Viability of Arthroaleuriosporous Fungus", G. F. Orr et al., (Environ, Life Sci. Div., U.S. Army Dugway Proving Ground, Dugway, Utah), Bulletin Torrey Botanical Club 1977, 104(1), 25-8.
"The Effect of Post-Infectional Potato Tuber Metabolites and Surfactants on Zoospores of Oomycetes," Jane E. Harris et al., (A.R.C. Food Res. Inst., Norwich, Engl.), Physiol. Plan Pathol., 1977, 11(2), 163-9.
"Eradication of the Perithecial Stage of Apple Scab with Surfactants," R. T. Burchill et al., (East Malling Res. Stn., Maidstone/Kent, Engl.), Ann. Appl. Biol. 1977, 87(2), 229-31.
"Effects on Some Surfactant Fungicides on Rhizobium Trifolii and Its Symbiotic Relationship with White Clover," D. J. Fisher et al., (Long Ashton Res. Stn., Univ. Bristol. Long Ashton/Bristol, Engl.), Ann. Appl. Biol., 1978, 90(1), 73-84.
"Effects of Fungicides and Surfactants on the Zoospores of Olpidium Brassicae," J. A. Tomlinson et al., (Natl. Veg. Res. Stn., Wellesbourne/Warwick, Engl. CV 35 9EF), Ann. Appl. Biol. 1979, 93(1), 13-19.
"Surfactants for the Control of Apple Mildew," Derek R. Clifford et al., (Long Ashton Res. Stn., Univ. Bristol, Bristol, Engl.), Pestic. Sci. 1975, 6(4), 409-18.
"Surfactants as Fungicides," F. R. Forsyth, Canadian Journal of Botany 42, (1964), pp. 1335-1347.

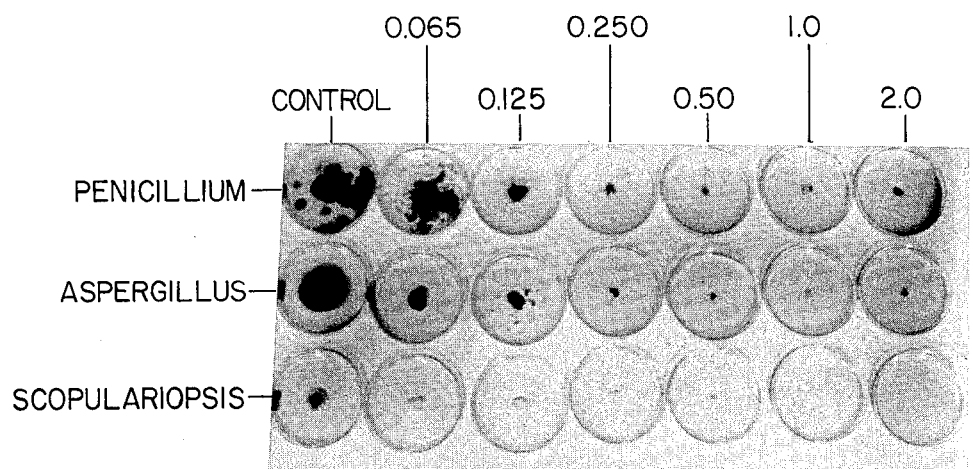
FIG. I

ANTI-FUNGAL METHODS AND AGENT

FIELD OF THE INVENTION

The field of the invention relates to anti-fungal methods and anti-fungal compositions. More particularly, this invention relates to a method for inhibiting the growth of fungi on surfaces and articles, a method for treating systemic, subcutaneous, cutaneous and superficial mycoses in humans and animals and anti-fungal compositions effective for carrying out the aforementioned methods. The compositions include lotions, creams, ointments, salves, powders, sprays, capsules, tablets, suppositories and/or suspensions and solutions for administration by any route.

BACKGROUND OF THE INVENTION

Of the estimated 50,000 to 200,000 species of fungi, only a few hundred are presently known to cause infectious disease in man and animals. Because of the biochemical and physiological differences among the fungi, bacteria and viruses, fungal diseases in animals and in humans are normally not treatable with anti-bacterial and anti-viral agents. To date, there are only a limited number of anti-fungal agents available to treat human and animal mycoses, such as griseofulvin and the polyene antibiotics such as amphotericin B, 5-Fluorocytosine (Flucytosine), miconazole and ketoconazole. These agents, however, do not provide effective treatment for all mycoses. For example, griseofulvin is effective only for superficial and subcutaneous mycoses and requires prolonged administration of weeks or months. While amphotericin B is effective for the treatment of many, but not all, systemic mycoses it is not effective for the treatment of superficial and cutaneous mycoses. Also amphotericin B often exhibits some toxicity.

Unfortunately, certain mycoses are not amenable to treatment with the existing anti-fungal agents and often are fatal to the hosts. The occurrences and debilitating effects of fungal diseases in humans and animals could be markedly reduced if a means for quickly combating the pathogenic fungal agent could be safely administered to the infected host or patient.

In addition to various methods and compositions presently known to be useful for treating human and animal mycoses, methods and compositions are presently known to be effective in combating fungal disease in plants. Because of the biochemical and physiological differences between plants and humans (and animals), methods and compositions for treating plants have not been adapted to humans and animals for the treatment of mycoses. Conversely, methods and compositions for treating human and animal mycoses have not been adopted to treating fungal disease in plants. For example, the mode of treatment for a plant mycosis is normally directed to inhibition of spore germination, or the elimination of spores. In contrast, although fungal spores are the usual causative agent for the invasion of the human or animal host, it is fungal yeast cells, fungal hyphae and fungal mycelium that deleteriously effects the health and well being of the human or animal host. Accordingly, once a human or animal host is infected with a fungal disease, inhibition of fungal spores and spore germination has little, if any, effect in curing the mycosis.

SUMMARY OF THE INVENTION

The present invention is directed to a method of anti-fungal treatment for humans and animals. One embodiment of the present invention is directed to a method for treating fungal infections of humans and animals which comprises administering to a human or animal having a fungal infection an effective anti-fungal dosage of a compound of the following formula:

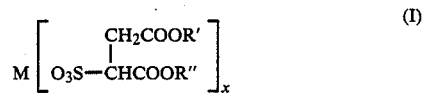

R' and R" are each independently a straight chain or branched chain alkyl group having from 5 to 8 carbon atoms, M is a physiologically compatible group selected from $NH_4$, Na, K, or Ca, and x is 1 when M is $NH_4$, Na or K, and x is 2 when M is Ca.

Another embodiment of the present invention is directed to a method for treating a systemic or localized fungal infection of animals and humans which comprises administering to the animal or human having a systemic or localized fungal infection an effective anti-fungal dosage of a compound of the above Formula (I). A further embodiment of the present invention is directed to a method for preventing a fungal infection in an animal or human which comprises administering to the animal or human an effective anti-fungal dosage of a composition of the above Formula (I).

An additional embodiment of the present invention is directed to a method of treating a superficial or cutaneous fungal infection in an animal or human comprising topically applying to the external surface of the human or animal a composition containing an effective anti-fungal amount of a composition of the above Formula (I). By external surface of a human or animal is meant the skin, eye surfaces, finger and toenails and mucous membranes.

In another embodiment of the present invention, the compound of Formula (I) is used in a method of disinfecting or sterilizing surfaces, such as kitchen, bathroom and hospital floors, walls, cabinets and counter tops, by spraying or wiping the surface with a solution containing an effective anti-fungal concentration of a composition of the above Formula (I).

BRIEF DESCRIPTION OF THE DRAWING

FIG. 1 is a photograph of fungal cultures of Scopulariopsis, Penicillium and Aspergillus treated with various concentrations of docusate sodium from 0 concentration (the control) to 2.0 mg/ml and incubated for five days at room temperature.

DETAILED DESCRIPTION

The anti-fungal agent of the present invention is a compound of the following formula:

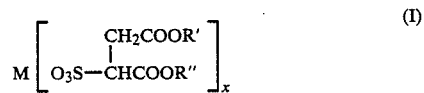

wherein R' and R" are each independently a straight chain or branched chain alkyl group of from 5 to 8 carbon atoms, M is a physiologically compatible group selected from NH4, Na, Ca, K and the like, and x is 1 when M is NH4, Na or K and x is 2 when M is Ca.

The M group and the dosage of the compound of Formula (I) are selected such that concentration of M in the human or animal host receiving the anti-fungal agent will be at a non-toxic concentration in the host. Normally for systemic applications and most topical applications, M will be Na, K and Ca.

The R' and R" groups can be the same or different. Preferably, however, R' and R" will be the same. Typical R' and R" groups include amyl, octyl and 2-ethylhexyl; preferably R' and R" are both 2-ethylhexyl. In the preferred embodiment of the present invention, M will be Na or Ca and most preferably M will be Na.

In the preferred embodiment of the present invention, the anti-fungal agent of Formula (I) is dioctyl sodium sulfosuccinate [(also known as 1,4 bis(2-ethylhexyl) sodium sulfosuccinate, docusate sodium, and DSS].

The effective dosage of the anti-fungal agent is provided to the animal and human host in a delivery system which assures a systemic or local concentration of between about 0.01 and 0.2 mg of the anti-fungal agent per ml of body fluids at the cellular level.

The term "systemic" as used herein with regard to concentration, means the concentration of the anti-fungal agent per ml of body fluids at the cellular level within the body generally. The term "local" as used herein with regard to concentration, means the concentration of the anti-fungal agent per ml of body fluids at the cellular level at a specific body site, for example, in a particular organ.

In accordance with the practice of the method of the present invention, fungal infections in human or animal hosts are susceptible to treatment by administering to the host an effective dosage of the above anti-fungal agent. Although the method of this invention is described below with respect to dioctyl sodium sulfosuccinate, practice of principles of this invention is contemplated with the anti-fungal agents of the above Formula (I) which are equivalent to docusate sodium, such as dioctyl calcium sulfosuccinate [1,4-bis(2-ethylhexyl) calcium sulfosuccinate] and dioctyl potassium sulfosuccinate [1,4-bis(2-ethylhexyl) potassium sulfosuccinate] and the like.

The term "treatment" or "treating" a fungal infection as used herein, means administering an anti-fungally effective amount of an agent of the above Formula (I) to a human or animal already infected. The term "preventing" a fungal infection means administering an anti-fungally effective amount of an agent of the above Formula (I) to a human or animal not already infected to thereby prevent infection. Administering an "anti-fungally effective" amount of an agent of the above Formula (I) to a human or animal, as used herein, means administering a sufficient amount of such an agent to obtain a systemic or local concentration of from about 0.01 to about 0.2 mg of the composition per ml of body fluids at the cellular level. The mode of action of docusate sodium on a fungi is not known. It could affect the permeability of the fungi cell wall or membrane, the fungi's respiration or metabolic processes, or the like. Whatever the mode, docusate sodium inhibits the growth of yeast cells, hyphae and mycelium.

Docusate sodium, which is a wax-like solid, is slowly soluble in water to a limited extent and freely soluble in organic solvents such as alcohol. Docusate sodium can be prepared by esterification of maleic anhydride with 2-ethylhexyl alcohol followed by addition of sodium bisulfite. The other compounds of Formula (I) can be prepared by esterification of maleic anhydride with the appropriate physiologically acceptable alcohol followed by the addition of the appropriate bisulfite salt, such as ammonium bisulfite, potassium bisulfite, and calcium bisulfite.

Docusate sodium is widely used as a wetting agent in a variety of industrial, pharmaceutical, cosmetic and food additive applications. For example, it is used in cocoa preparations, evaporated milk, cold packed cheese food, cream cheese and french dressing as an additive. As a pharmaceutical it is used as a stool softening agent. To be effective as an anti-fungal agent in accordance with the practice of the principles of the method of the present invention, the concentration of docusate sodium in the body fluids of the human and animal host at the cellular level must be at least about 0.01 mg of docusate sodium per ml of such fluid. This requires a dosage regimen of from about 5 mg to about 35 gms per day of docusate sodium in a delivery system which assures a systemic or local concentration of at least about 0.01 mg of docusate sodium per ml of body fluids at the cellular level.

Preferably, the concentration of docusate sodium in fluids at the cellular level is no greater than about 0.2 mg per ml of such fluids to provide a safety factor thereby ensuring that there are no toxic side effects to the host. While docusate sodium is used as a food additive and as a pharmaceutical stool softening agent, it is known that such uses do not provide a systemic or local concentration of from about 0.01 mg to about 0.2 mg of docusate sodium per ml on a cellular level as is required for practice of the present invention.

Docusate sodium can be administered orally, intravenously, subcutaneously, intramuscularly, intercutaneously, topically or by inhalation or instillation into a body site or cavity. Regardless of the type of administration, it may be dispersed in a pharmaceutically acceptable carrier. For example, when administered orally, it can be in tablet or capsule carriers, which can include components such as excipients, bulking agents, lubricants, disintegrants, solubilizing solvents, dyes and the like. It can also be administered orally in a suitable liquid carrier. For example, a carrier comprising ethanol and/or glycerol or the like. The term "carrier" further includes vehicles or materials useful in preparing an injection or intravenous form of docusate sodium such as isotonic saline-type solutions, isotonic dextrose-type solutions and the like. When used topically to treat superficial and cutaneous mycoses, it may be formulated into a pharmaceutically acceptable composition, such as, for example, a lotion, cream, emulsion, salve and the like. It can also be applied topically as a powder or dry or liquid spray. Additionally, it can be provided for administration in pharmaceutically acceptable mouthwash formulations for oral and laryngeal mycoses.

In further examples of vehicles for administration of docusate sodium, it may be provided in a pharmaceutically acceptable carrier for use an aerosol spray for bronchial inhalation therapy, for instance. It may also be provided as the active anti-fungal ingredient in an anti-fungally effective powder. Docusate sodium may also be provided in a cleanser formulation for use in disinfecting body surfaces or as a sanitizer for disinfecting surfaces such as bathroom and kitchen fixtures and the like.

In a further exemplary embodiment of using docusate sodium as an anti-fungal agent, a material such as a cellulosic web, can be used as a substrate or carrier for an effective amount of docusate sodium. Thus, for example, a facial tissue, a bathroom tissue or a hand towel or the like may be impregnated with an anti-fungally effective amount of docusate sodium. Use of such impregnated tissues or towels can result in controlling spread of fungal mycoses.

For example, non-woven substrates such as wet-creped hand towels and spunbonded and meltblown polymeric web commonly used in disposable hospital items such as surgical drapes, gowns, bedsheets, pillow cases and textile materials and the like can be impregnated with docusate sodium. Hygienic face masks used by persons suffering from respiratory illness or by persons working in a dusty environment where the dust is contaminated with pathogenic fungal spores can be impregnated with an anti-fungally effective amount of docusate sodium. Further, disposable diapers can be impregnated with docusate sodium as well as tampons and intravaginal sponges and the like. Docusate sodium may also be provided in an appropriate carrier as a vaginal douche.

In one exemplary embodiment of the present invention, docusate sodium is provided in a time/sustained-release capsule form as is known in the art. In such form, from about 5 mg to about 35 gms of docusate sodium is administered per day to the human or animal host either as a curative for an existing mycosis or as a prophylactic to mycoses. The most common route of infection for fungal diseases arises from spore inhalation into the mouth, throat and/or lungs of a human or animal host. Less common, infections can be acquired through invasion of the fungi through cuts and lesions in the external surface of the human or animal host. Humans and animals subject to a higher incidence of fungal diseases can effectively employ docusate sodium as a prophylactic for mycotic infections. For example, people who work and live amidst bird and pigeon droppings can be administered an effective dosage of docusate sodium on a continuing basis as a prophylactic against *Cryptococcus neoformans* (cryptococcosis). Individuals exposed to cave dust or soil contaminated with droppings of bats and barnyard soil heavily contaminated with bird droppings can be administered an effective dose of docusate sodium to act as a prophylactic against *Histoplasma capsulatum* (histoplsmosis). Moreover, persons in the southwestern portion of the United States can be administered an effective dosage of docusate sodium to act as a prophylactic against *Coccidioides immitis* (coccidioidomycosis). In addition, farmers and others who handle decaying vegetation and persons who maintain and repair air conditioning systems, for example, can be administered an effective dosage of docusate sodium to act as a prophylactic against *Aspergillus fumigatus* (aspergillosis). In addition, the general human and/or animal population of a given geographic area can be administered an effective dosage of docusate sodium at times or during the season when the soil is contaminated with high concentrations of spores of known pathogenic fungi.

When docusate sodium is administered as a treatment for systemic or local mycoses, the dosage regimen is adjusted such that the systemic or local concentration of docusate sodium in the body fluids of the human or animal host at the cellular level is from about 0.01 to about 0.2 mg per ml of fluid. The treatment is continued until the infection is healed. When docusate sodium is administered as a treatment for superficial and cutaneous mycoses, docusate sodium may be topically administered to fungal lesions at the site of infection on the external surface of the human or animal host, preferably at least daily, until the infection is healed. For some superficial and cutaneous mycoses, topical treatment is augmented with systemic treatment as described herein for the treatment of systemic mycotic infections.

For the treatment of systemic mycosis and subcutaneous mycosis, the preferred method of treatment is internal administration of a docusate sodium to effect a concentration of between 0.01 and 0.2 mg of docusate sodium per ml of body fluid at the cellular level. For cutaneous mycosis and superficial mycosis, the preferred route of administration is by topical application of the docusate sodium as a spray, lotion, cream, salve, ointment or powder.

EXAMPLE 1

Topical Administration - Lotion

An exemplary embodiment of lotion prepared for topical administration for treating fungal infection in accordance with practice of principles of this invention comprises 0.2% wt/wt docusate sodium, 5% wt/wt mineral oil, 4.5% wt/wt stearic acid, 3.5% wt/wt cetyl alcohol, 1.5% wt/wt triethanolamine, 0.15% wt/wt methylparaben, 0.05% wt/wt propylparaben with the remainder being sterile (deionized and filtered) water.

The lotion is prepared in two phases, phase A which includes mineral oil, stearic acid, cetyl alcohol, and propylparaben and phase B which includes sterilized water, triethanolamine, methylparaben and docusate sodium.

To prepare the lotion an appropriate amount of mineral oil is metered into a jacketed stainless steel vessel. Into the same vessel an appropriate amount of each of stearic acid, cetyl alcohol and propylparaben is measured. Moderate propeller agitation is provided and phase A (oil phase) is heated to 70 to 75° C. Mixing is continued until all solids are melted and a clear solution is obtained. Phase B is then obtained by weighing an appropriate amount of water into a jacketed stainless steel vessel (main mixing vessel) which is provided with both a propeller and a sweep agitation. Into the same vessel an appropriate amount of each of triethanolamine, methylparaben and docusate sodium is added. With gentle propeller agitation phase B is brought to 72°–77° C. to obtain a clear solution. Phase A is then added to phase B which is at 72°–77° C., in the main mixing vessel with continued propeller agitation. Mixing is continued for 20 minutes with the combined phases at about 70° to about 77° C. The batch is then cooled by introducing cooling water into the jacket of the vessel. Cooling is continued with moderate propeller agitation. When the batch begins to thicken agitation is continued until batch temperature reaches about 25° to about 30° C. A sample is then taken from both the top and bottom of the batch for quality control analysis.

The product is then ready to be placed into containers for topical application.

A person who has a Trichophyton infection applies the lotion to the scalp periodically. In one embodiment the lotion is applied 3 times a day. The treatment is continued until the condition is healed.

While the above Example illustrates the use of one exemplary lotion formulation, compositions are contemplated which include pharmaceutically acceptable carriers other than those of this embodiment. Additionally, the percentage of docusate sodium used can be varied. For example, lotion formulations having as little a 0.001% to greater than 1% by weight docusate sodium are contemplated.

EXAMPLE 2

Topical Administration - Mouthwash

An exemplary embodiment of a mouthwash prepared for topical administration for treating or inhibiting fungal infection in accordance with practice of principles of this invention comprises 0.2% wt/wt docusate sodium, 5.0% wt/wt sorbitol solution, 10.0% wt/wt ethanol, and the remainder sterilized (deionized and filtered) water.

A person having an active lesion in the oral cavity from *Candid albicans* (thrush) takes from about 1 teaspoon full to about 4 teaspoons full of the mouthwash and places it into his mouth (oral cavity). The mouthwash is vigorously swished around in the mouth to thereby contact the total surface of the oral cavity and the mycotic lesions with an anti-fungally effective amount of docusate sodium. After one minute or so the mouthwash is spit out. The procedure is repeated at intervals of several hours until the lesions are healed.

While the above example illustrates the use of one exemplary mouthwash formulation, formulations can be used which include pharmaceutically acceptable carriers other than those of this embodiment. Additionally, the percentage of docusate sodium used can be varied. For example, mouthwash formulations having as little as 0.001% to greater than 1% by weight docusate sodium are contemplated.

EXAMPLE 3

Topical Administration - Cleanser

An exemplary embodiment of a cleanser prepared for topical administration for treating or preventing fungal infection in accordance with practice of principles of this invention comprises, by weight, 23.3% sodium ($C_{14}$–$C_{16}$) olefin sulfonate, 5% myristamine oxide, 1% cocamidopropylbetaine, 3.5% lauramid DEA, 0.25% polyquaternium-7, 0.% NaCl, 0.2% dioctyl sodium sulfosuccinate, a fragrance and a preservative with the remainder being sterile water. Sufficient citric acid is added to the resulting cleanser to bring the pH of the cleanser to about 7.

The cleanser is used to wash the external surface of the body for inhibiting fungal growth on the surface which the cleanser contacts.

While the above example illustrates the use of one exemplary cleanser formulation, formulations can be used which include pharmaceutically acceptable carriers other than those of this embodiment. Additionally, the percentage of docusate sodium used can be different. For example, cleanser formulations having as little as 0.001% to greater than 1% by weight docusate sodium are contemplated.

EXAMPLE 4

Surface Sterilization

An exemplary embodiment of a sanitizer prepared for disinfecting surfaces, such as bathroom and kitchen fixtures and the like, in accordance with practice of principles of this invention comprises about 0.2% wt/wt docusate sodium, about 10.0% wt/wt ethanol and the balance sterile water.

The solution is sprayed onto a bathroom fixture, for example, onto a toilet seat, to inhibit fungal growth on the toilet seat.

While the above example illustrates the use of one exemplary sanitizer composition, compositions comprising other ingredients can be used. Additionally, the percentage of docusate sodium can be different. For example, sanitizers having as little as 0.001% to greater than 10% by weight docusate sodium are contemplated.

EXAMPLE 5

Systemic Administration Time/Sustained-Release Capsule

In an exemplary embodiment of practice of this invention for systemic treatment of mycoses, docusate sodium is provided in a time/sustained-release capsule form as is known in the art. From about 5 mg to about 35 gms of docusate sodium in such time/sustained-release capsule form is administered per day to a person who has cryptococcosis. The dosage or form of drug administered is such that the systemic or local concentration of docusate sodium at the cellular level of the person being treated is from between 0.01 and 0.2 mg per ml. The treatment is continued during the course of the infection.

EXAMPLE 6

Systemic Treatment - Tablet Form

In an exemplary embodiment of practice of this invention for systemic treatment, docusate sodium is administered in tablet form to a person to prevent disease due to *Candida albicans*. The dosage is such that the systemic or local concentration of docusate sodium at the cellular level is maintained at from about 0.01 to 0.2 mg per ml.

EXAMPLE 7

Facial Tissue Impregnated With Docusate Sodium

A cellulosic web facial tissue is impregnated with an anti-fungally effective amount of docusate sodium. For example, docusate sodium is present in an amount of from about 0.001% to about 3% or more based on the total weight of docusate sodium and the weight of the tissues. A fungal agent which contacts the tissue, for example a fungal spore, is inactivated by such contact.

EXAMPLE 8

Cytotoxicity of Docusate Sodium in Solutions Free of Serum

The cell lines used to evaluate cytotoxicity of docusate sodium were MA-104 derived from monkey kidneys, HeLa derived from human uterine carcinoma and primary fibroblasts from human foreskin. The cells were grown to confluency in 60×15 mm dishes. The cell monolayers were washed free of growth medium and 5 ml of serum-less growth medium containing docusate sodium at various concentrations was added. The cultures were incubated 24 hours at 37° C. and the cells then examined microscopically for cytotoxic effects (CTE). Controls were done in the same manner except that they were not exposed to docusate sodium.

Table 1 lists the cytotoxicity of docusate sodium with regard to selected cell lines in cell culture.

TABLE 1

| Solution | (1) | (2) | (3) | (4) | (5) |
|---|---|---|---|---|---|
| mg/ml docusate sodium | 0 | 0.2 | 0.1 | 0.05 | 0.01 |
| MA-104 (toxicity) | 0* | 4+** | 4+ | 4+ | 0 |
| HeLa (toxicity) | 0 | 4+ | 4+ | 4+ | 0 |
| Foreskin (toxicity) | 0 | 4+ | 4+ | 4+ | 0 |

*Cells had normal morphology
**>90% of cells showed CTE.

As is shown in Table 1, docusate sodium was toxic to the cells when the concentration of docusate sodium in the solution described in this example was between 0.1 and 0.05 mg/ml.

EXAMPLE 9

Cytotoxicity of Docusate Sodium in Solutions Containing Serum

The same procedure that was used for Example 8 was used for this example except that the medium used for growing the cells contained 2% by volume fetal calf serum.

Table 2 lists the cytotoxic effect of docusate sodium at various concentrations in selected cell lines in the cell cultures of this Example.

TABLE 2

| Solution No. | (1) (control) | (2) | (3) | (4) | (5) |
|---|---|---|---|---|---|
| mg/ml docusate sodium | 0 | 0.04 | 0.03 | 0.02 | 0.01 |
| MA-104 (Cytotoxic effect) | 0* | 0 | 0 | 0 | 0 |
| HeLa (Cytotoxic effect) | 0 | 4+** | ±c*** | 0 | not avail. |
| Foreskin (Cytotoxic effect) | 0 | 4+ | 4+ | ±c | 0 |

*Cells have normal morphology
**>90% of cells showed CTE.
***less than 10% of cells showed CTE.

The results presented in Table 2 indicate that the presence of serum reduced the cytotoxicity of docusate sodium. The results also indicated that MA-104 cells were less sensitive to docusate sodium than were HeLa and foreskin fibroblast cells.

EXAMPLE 10

Inhibition of the Growth of Candida Albicans

*Candida albicans* is a yeast and is the causative agent of thrush in humans and is a cause of vaginal infections, urinary tract infections, and infections at other body sites. The growth inhibition effects of docusate sodium on *C. albicans* are determined in broth culture using trypticase soy broth (TSB) which is a medium which supports growth of a wide variety of microorganisms. TSB was sterilized by autoclaving and filter sterilized docusate sodium in distilled water was added to the sterile TSB at the concentrations shown in Table 3. The cultures were inoculated and incubated at 30° C. for 72 hours. Growth in the cultures was checked at 24 hour intervals.

TABLE 3

| Mg/ml docusate sodium | Incubation time in hours | | | |
|---|---|---|---|---|
| | 0 | 24 | 48 | 72 |
| 2.0 | 0.320 | 0.470 | 0.620 | 0.780 |
| 1.0 | 0.290 | 0.310 | 0.450 | 0.610 |
| 0.5 | 0.240 | 0.315 | 0.420 | 0.730 |
| 0.25 | 0.220 | 0.345 | 0.600 | 0.720 |
| 0.12 | 0.230 | 0.440 | 0.700 | 0.950 |
| 0.06 | 0.185 | 0.610 | 1.10 | 0.920 |
| 0 | 0.175 | 0.720 | 0.90 | 0.980 | a. Growth recorded as absorbance at 540 nm

As shown in Table 3 growth of *C. albicans* was inhibited at concentrations of docusate sodium above 0.06 mg/ml.

EXAMPLE 11

Inhibition of the Growth of Mucor, Scopulariopsis, Penicillium and Aspergillus

The nature of fungal growth required that a different experimental approach from that of Example 10 be used to determine the growth inhibition effects of docusate sodium on fungi. For these experiments potato dextrose agar plates containing different concentrations of docusate sodium were inoculated in the center of the agar with Scopulariopsis, Penicillium and Aspergillus. The cultures were then sealed with PARAFILM brand film and incubated at room temperature for five days. Since growth could not be measured by absorbance visual comparisons were made. The experimental results are shown in FIG. 1. The results shown in FIG. 1 demonstrate the growth of fungi was inhibited at all concentrations of docusate sodium. The fungi differed in sensitivity to docusate sodium with Penicillium, being least sensitive and Aspergillus and Scopulariopsis being more sensitive. The results to date indicate that docusate sodium is fungistatic. Microscopic examination of the fungal colonies indicated that the growing tips of the fungal mycelia (filaments) are sensitive to docusate sodium. Similar tests were conducted with Mucor. Mucor growth was inhibited at all concentrations of docusate sodium tested.

Although the embodiments of the method of this invention are described above with reference to Candida, Mucor, Scopulariopsis, Penicillium and Aspergillus the methods and compositions of this invention can be used for treatment of other fungal infections as well. For example, fungal infections caused by *Blastomyces dermatitidis, Histoplasma capsulatum, Coccidioides immitis, Paracoccidioides brasiliensis, Sporothrix schenckii, Cryptococcus neoformans,* and *Fonsecaea pedrosoi* and the like can be treated in accordance with these methods.

The above descriptions of exemplary embodiments of methods for treating fungal infections are for illustrative purposes. Because of variations, which will be apparent to those skilled in the art, the present invention is not intended to be limited to the particular embodiments described above. The scope of the invention is defined in the following claims.

What is claimed is:

1. A method for treating fungal infections of animals and humans comprising administering to an animal or human having a fungal infection an effective anti-fungal dosage of a compound of the following formula:

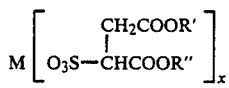

ps wherein R' and R" are each independently a straight chain or branched chain alkyl group of from 5 to 8 carbon atoms, M is Na, Ca or K, and x is 1 when M is Na or K, and x is 2 when M is Ca.

2. The method according to claim 1 wherein the anti-fungal compound is dioctyl sodium sulfosuccinate.

3. The method according to claim 2 wherein the effective anti-fungal dosage provides a concentration of dioctyl sodium sulfosuccinate of from about 0.01 to about 0.2 mg per ml of body fluids of said humans and animals at the cellular level.

4. The method according to claim 2 wherein the effective anti-fungal dosage is from about 5 mgs to about 35 gms of dioctyl sodium sulfosuccinate per day in a delivery system which assures a systemic or local concentration of from about 0.01 to about 0.2 mg of dioctyl sodium sulfosuccinate per ml of body fluids on a cellular level.

5. A method of treating a systemic or localized fungal infection of humans and animals comprising orally administering to humans and animals having a systemic or localized fungal infection an effective anti-fungal dosage of a compound of the following formula:

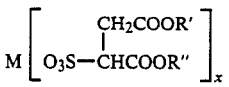

wherein R' and R" are each independently a straight chain or branched chain alkyl group of from 5 to 8 carbon atoms, M is Na, Ca or K, and x is 1 when M is Na or K, and x is 2 when M is Ca.

6. The method according to claim 5 wherein the anti-fungal compound is dioctyl sodium sulfosuccinate.

7. The method according to claim 5 wherein the effective anti-fungal dosage derives a concentration of dioctyl sodium sulfolsuccinate of from about 0.01 to about 0.2 mg per ml of body fluids of said humans and animals at the cellular level.

8. The method according to claim 6 wherein the effective anti-fungal dosage is from about 5 mgs to about 35 gms of dioctyl sodium sulfosuccinate per day in a delivery system which assures a systemic or local concentration of between about 0.01 and 0.2 mg of dioctyl sodium sulfosuccinate per ml of body fluids on a cellular level.

9. The method according to claim 5 wherein the systemic or localized fungal infection is cryptococcosis.

10. The method according to claim 5 wherein the systemic or localized fungal infection is candidiasis.

11. The method according to claim 5 wherein the systemic or localized fungal infection is aspergillosis.

12. The method according to claim 5 wherein the systemic or localized fungal infection is scopulariopsis.

13. The method according to claim 5 wherein the systemic or localized fungal infection is mucormycosis.

14. A method for treating a topical fungal infection of humans and animals comprising topically applying to the humans and animals at the site of the fungal infection a composition containing an effective anti-fungal amount of a compound of the following formula:

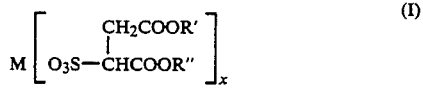

wherein R' and R" are each independently a straight chain or branched chain alkyl group of from 5 to 8 carbon atoms, M is Na, Ca or K, and x is 1 when M is Na or K, and x is 2 when M is Ca.

15. The method according to claim 14 wherein the anti-fungal compound is dioctyl sodium sulfosuccinate.

16. The method according to claim 15 wherein the composition has a dioctyl sodium sulfosuccinate concentration of from about 0.01 to about 0.2 mg per ml of said composition.

17. The method according to claim 15 wherein the composition is applied at least daily during the course of the infection.

18. The method according to claim 14 wherein the topical fungal infection is candidiasis.

19. The method according to claim 14 wherein the topical fungal infection is a penicillium infection.

20. The method according to claim 14 wherein the topical fungal infection is aspergillosis.

21. The method according to claim 14 wherein the topical fungal infection is caused by Mucor.

22. The method according to claim 14 wherein the topical fungal infection is caused by Scopulariopsis.

23. A method for inhibiting the growth of a selected fungi within a human host comprising the steps of contacting the fungi with dioctyl sodium sulfosuccinate by providing a dioctyl sodium sulfosuccinate concentration in the fluids of the human host of from about 0.01 to about 0.2 mg per ml of said fluids at the cellular level.

24. A method for inhibiting the growth of a selected fungus in cells in human and animal hosts, the method comprising the steps of administering a systemic dosage of dioctyl sodium sulfosuccinate to the human and animal host for contacting such cells in the human or animal host with said dioctyl sodium sulfosuccinate in body fluids, the dioctyl sodium sulfosuccinate being provided in such body fluids at a systemic concentration of from about 0.01 to about 0.2 mg per ml of said fluid solution at the cellular level.

25. The method according to claim 24 wherein the effective dosage is from 5 mg to about 35 gms per day in a delivery system which provides a systemic concentration of between about 0.01 and 0.2 mg of said dioctyl sodium sulfosuccinate per ml of body fluids on a cellular level.

26. The method according to claim 25 wherein the fungus is selected from the group consisting of Cryptococcus, Candida, Aspergillus, Phycomycetes, Scopulariopsis and Penicillium.

* * * * *